United States Patent [19]

Dillon et al.

[11] Patent Number: 4,886,073
[45] Date of Patent: Dec. 12, 1989

[54] SHOULDER STRENGTH ADDUCTION DEVICE

[75] Inventors: George A. Dillon, Westlake Village; Max Van Mastrigt, San Jose, both of Calif.

[73] Assignee: Dillon/Quality Plus, Inc., Camarillo, Calif.

[21] Appl. No.: 182,397

[22] Filed: Apr. 18, 1988

[51] Int. Cl.$^4$ .............................................. A61B 5/22
[52] U.S. Cl. ...................................... 128/774; 73/379; 272/135
[58] Field of Search ................ 128/774, 777, 781–782; 73/379–381; 272/116–117, 125–128, 134–136, 141, 143

[56] References Cited

U.S. PATENT DOCUMENTS

| | | | |
|---|---|---|---|
| 3,971,255 | 7/1976 | Varney et al. | 272/143 X |
| 4,023,796 | 5/1977 | Kusmer | 272/125 X |
| 4,210,323 | 7/1980 | Feather | 272/126 X |
| 4,374,588 | 2/1983 | Ruggles | 272/125 X |
| 4,432,543 | 2/1984 | Normandin | 272/126 |
| 4,580,778 | 4/1986 | Van Noord | 272/135 X |

Primary Examiner—Angela D. Sykes
Attorney, Agent, or Firm—Kelly, Bauersfeld & Lowry

[57] ABSTRACT

An improved shoulder strength adduction device is provided for use in determining the strength of a person's shoulder musculature. The device comprises a pair of hand grips connected by pivotal scissors frames to a support bar and a load bar, with a force gauge unit being mounted between the support and load bars. Exertion of manual adduction force to move the hand grips toward each other is effective to urge the support and load bars toward each other, whereby the adduction force can be detected and displayed by the force gauge unit to provide a direct reading of shoulder or upper body strength. The device includes a variety of mechanical improvements designed to enhance ease of use while achieving increased force indicating accuracy.

18 Claims, 2 Drawing Sheets

SHOULDER STRENGTH ADDUCTION DEVICE

BACKGROUND OF THE INVENTION

This invention relates generally to devices for testing and indicating the strength of selected muscles or muscle groups in humans. More specifically, this invention relates to an improved device for testing and indicating the strength of a person's shoulder musculature in a relatively simple yet accurate and repeatable manner.

In recent years, some employers in both the public and private sectors have established specific physical strength criteria which must be met by persons seeking to obtain or maintain employment in certain physically demanding occupations. For example, various state and local governments have established thorough physical performance standards designed to insure that its law enforcement officers, fire fighting personnel, etc., possess sufficient physical strength capabilities to perform their anticipated rigorous job duties in a safe and efficient manner. In addition, many private sector employers such as manufacturing concerns and the like have required employees to demonstrate certain minimum physical strength capabilities before permitting an employee to undertake a physically demanding job position. Accordingly, there has arisen a need for reliable testing equipment designed to measure the strength capabilities of various muscle groups in individuals.

As one common example, employers frequently require prospective or current employees to demonstrate minimum upper body strength abilities before allowing those employees to engage in physically demanding tasks. In general terms, a person's upper body strength is indicated by the overall strength of the shoulder musculature, substantially independent of a person's arm, hand, or wrist strength. In the past, attempts to quantify the upper body strength of an individual have primarily involved weight lifting techniques wherein the individual is required to lift a specified minimum weight to qualify for certain jobs. However, weight lifting techniques do not satisfactorily isolate the shoulder musculature from other muscle groups, such as the arm, hand, and wrist muscles, and thus such weight lifting techniques do not provide an accurate method to quantify or compare the upper body strength in individuals. Moreover, lifting of weights subjects the person being tested to potential injury if overexertion is required to lift a minimum weight required to meet occupational criteria.

There exists, therefore, a significant need for an improved muscle group strength testing device designed particularly for use in testing upper body strength in individuals, wherein the improved testing device is easy to use and provides a reliable, accurate, and repeatable shoulder strength reading. The present invention fulfills these needs and provides further related advantages.

SUMMARY OF THE INVENTION

In accordance with the invention, an improved shoulder strength testing device is provided for use in determining the upper body strength capabilities of an individual. The testing device comprises a lightweight frame adapted for minor adduction displacement and to measure the adduction force with a force gauge unit which provides a direct reading of a person's shoulder strength. The testing device is constructed for substantially isolating the shoulder musculature from other muscle groups and further to provide accurate, repeatable shoulder strength readings.

In accordance with a preferred form of the invention, the testing device comprises a pair of generally parallel hand grips connected between upper and lower scissors frames each including a pair of pivotally interconnected frame links. The hand grips are connected to the rear ends of the frame links in a manner permitting hand grip rotation respectively about the longitudinal axes of the hand grips to prevent application of significant torque forces to the device when the hand grips are pressed together for adduction displacement. The frame links of the upper and lower scissors frames are pivotally interconnected by a common pivot pin which includes spacer means for maintaining the scissors frames in substantially parallel relation to correspondingly permit the frame links to be constructed from lightweight components.

The forward ends of the frame links opposite the hand grips are secured respectively to a generally parallel and upright support bar and load bar. The force gauge unit is mounted on the support bar and includes a reaction arm subjected to minor displacement by the load bar in response to an adduction force applied when the hand grips are pressed together by a person being tested. An adjustable calibration screw on the load bar is retained in engagement with a load ball which is pressed in turn against a load cell platform on the reaction arm when the hand grips are pressed toward each other. A stop plate on the scissors frames prevents significant frame displacement such that the load ball is captured between the calibration screw and the load cell platform at all times. Moreover, the load bar is pivotally mounted onto the scissors frames to insure self aligning engagement between the calibration screw and the load ball.

In use, the person being tested holds the hand grips in an upright position generally at sternum level and then presses the hand grips toward each other with an adduction force. The support and load bars respond by undergoing a slight adduction displacement which presses the calibration screw against the load ball which presses in turn against the load cell platform on the reaction arm. As a result, the reaction arm undergoes a corresponding displacement which is detected and quantified by the force gauge unit as a direct readable indication of the strength of the person's shoulder muscles.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figures 1, 2, 3:
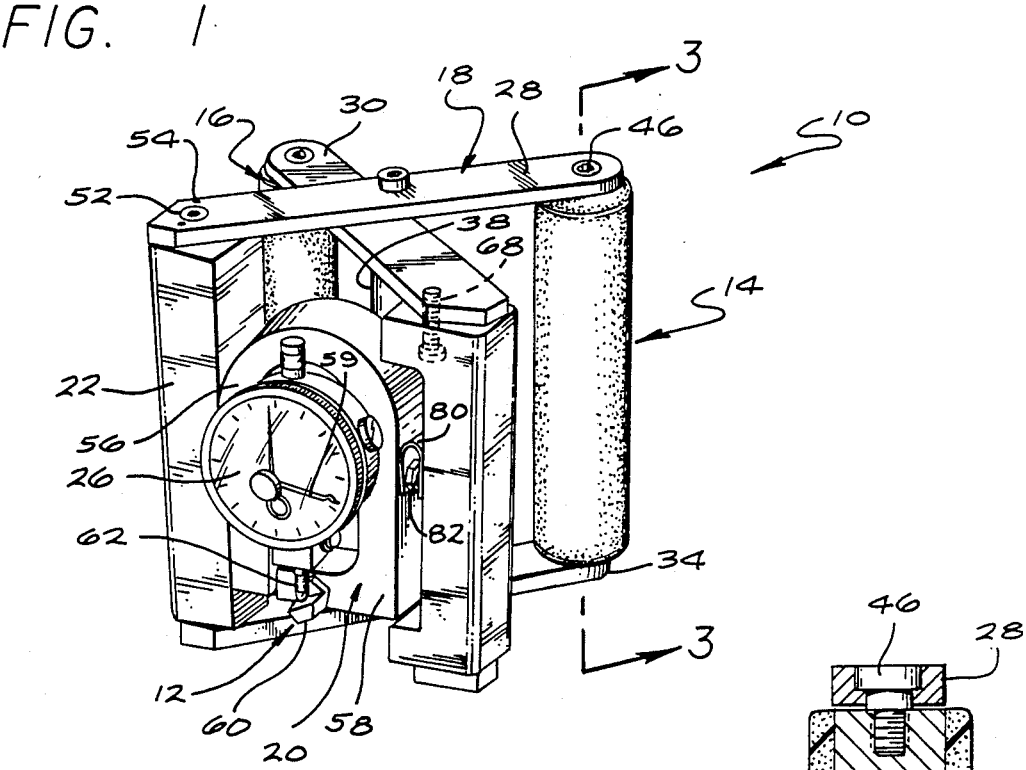
FIG. 1 is a perspective view depicting a shoulder strength adduction device embodying the novel features of the invention.
FIG. 2 is a top plan view of the shoulder strength adduction device.
FIG. 3 is an enlarged vertical sectional view taken generally on the line 3—3 of FIG. 1.
Figure 4:
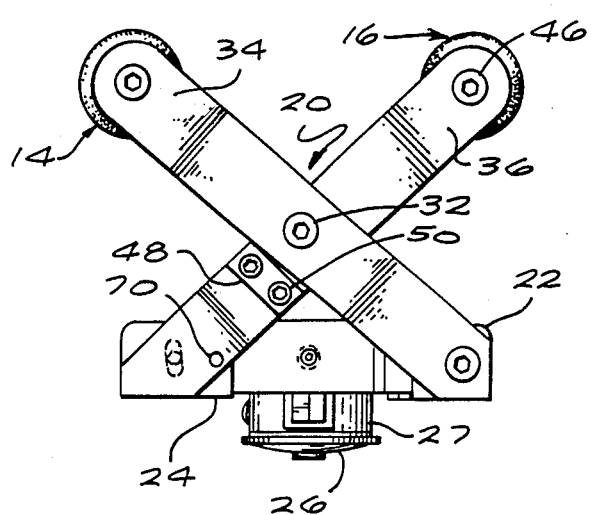
FIG. 4 is a bottom plan view of the device.

As shown in the exemplary drawings, an improved shoulder strength adduction device referred to generally by the reference numeral 10 is provided for use in testing the upper body strength of an individual. The device 10 comprises a relatively lightweight mechanical frame carrying a force gauge unit 12 for providing a direct reading of a person's shoulder strength when the frame is subjected to an adduction force.

The shoulder strength adduction device 10 is particularly designed as a simple, easy to use test device to determine upper body strength capabilities in applicants for certain occupations which require minimum strength levels for adequate job performance. The testing device 10 effectively isolates the shoulder musculature of a person being tested from other muscle groups, particularly such as the hand and arm, to provide an accurate indication of peak static isometric shoulder strength. Importantly, the device 10 is designed to insure consistent operation by many different individuals, whereby the device may be used with confidence to provide a standard of comparison between individuals.

As shown generally in FIGS. 1 and 2, the shoulder strength adduction device 10 comprises left and right hand grips 14 and 16 interconnected via the mechanical frame with the force gauge unit 12. In general terms, these hand grips 14 and 16 are coupled respectively to the force gauge unit 12 by means of upper and lower scissors frames 18 and 20. These scissors frames 18 and 20 carry a forward support bar 22 and a load bar 24 on opposite sides of the force gauge unit 12. Adduction forces applied to the hand grips 14 and 16 by pressing the hand grips toward each other are applied by the support and load bars 22 and 24 to the force gauge unit 12. As will be described in more detail, the force gauge 12 responds to the adduction forces to provide a direct and visible read-out in pounds or other suitable force units on a visible read-out dial 26 of a force gauge 27.

Figure 5:
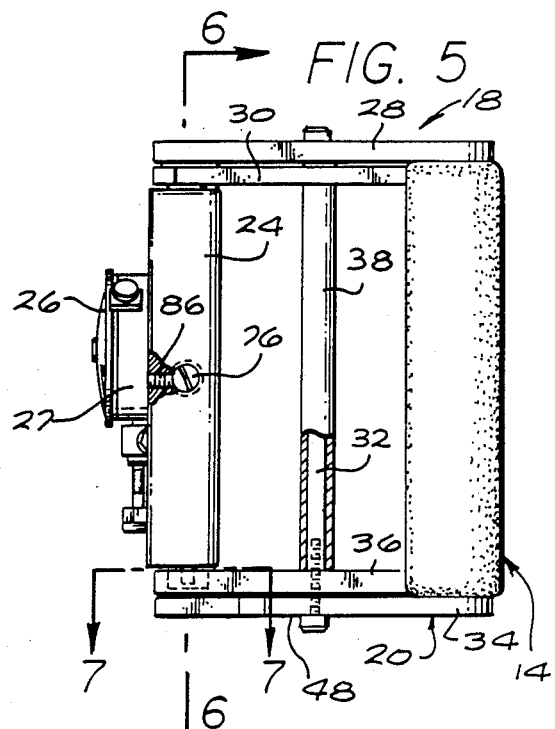
FIG. 5 is a right side elevation view of the device, with portions broken away to illustrate construction details thereof.

More specifically, the upper scissors frame 18 comprises a pair of frame links 28 and 30 which are pivotally interconnected generally at a midpoint position by an upright pivot pin 32. Similarly, the lower scissors frame 20 comprises another pair of frame links 34 and 36. These lower frame links 34 and 36 are pivotally interconnected generally at midpoint positions by the same pivot pin 32 (FIG. 5) which projects vertically between the upper and lower frames 18 and 20. An elongated spacer sleeve 38 is carried about the pivot pin 32 at a position between the upper and lower frames and cooperates with an enlarged upper head and lower nut on the pivot pin 32 to maintain the vertical spacing between the frames without significant distortion when subjected to relatively high adduction forces during use of the device. Accordingly, relatively lightweight frame link components can be used.

The left and right hand grips 14 and 16 are rotatably mounted at the rear ends of the scissors frames 18 and 20 such that the hand grips are vertically oriented and rotatable about generally parallel vertical axes. More particularly, with reference to the left hand grip 14 shown in more detail in FIG. 3, each hand grip comprises an elongated rod member 40 carrying an outer cushioned grip member 42 of foam rubber or the like. Shoulder screws 46 are fitted through the ends of the frame links 28 and 34 for threaded reception into the upper and lower ends of the rod member 40. That is, in the case of the left hand grip 14 as viewed in FIG. 3, the hand grip is connected between the rear ends of the frame links 28 and 34. The right hand grip 16 is similarly constructed and connected between the rear ends of the frame links 30 and 36. Accordingly, pressing movement of the hand grips 14 and 16 toward each other displaces the forward ends of the several frame links toward each other. Importantly, a stop plate 48 is fastened by screws 50 or the like to the underside of the frame link 36 in a position closely adjacent to the other lower frame link 34, and in generally the same plane as the link 34 to restrict the pivoting displacement of the upper and lower frames 18 and 20 to a small angular increment, such as about five to ten degrees.

The forward ends of the frame links 28 and 34 are suitably secured by screws 52 or the like respectively to upper and lower ends of the support bar 22. Additional set pins 54 may protrude through these frame links 28 and 34 to insure precision angular setting of the support bar 22 with respect thereto.

The force gauge unit 12 is mounted in turn an inboard face of the support bar 22. While this force gauge unit 12 may take any convenient form, one preferred gauge construction corresponds with the gauge shown and described in U.S. Pat. No. 3,370,458, which is incorporated by reference herein. More particularly, the illustrative force gauge unit 12 includes a base member 56 mounted onto the support bar 22 by a screw 44, with a washer 45 or the like interposed between the support bar 22 and the base member 56 to provide improved loading symmetry to the gauge. A reaction arm 58 is joined to the base member 56 in operative association with the load bar 24, wherein the reaction arm 58 transmits adduction forces to the force gauge 27 mounted on the base member 56. To this end, an angled cam member 60 on the reaction arm 58 is contacted by a probe 62 projecting downwardly from the force gauge 27 such that lateral deflection of the reaction arm 58 results in an altered dial reading on the force gauge 27. A peak load hand 59 (FIG. 1) is conveniently included on the gauge to provide a peak force reading. Alternately, other types of force gauges or meters such as digital equipment can be used, if desired.

Figure 7:
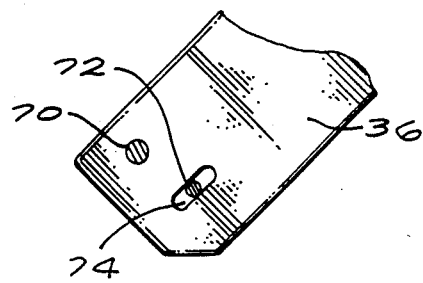
FIG. 7 is an enlarged fragmented horizontal sectional view taken generally on the line 7—7 of FIG. 5.
Figure 6:
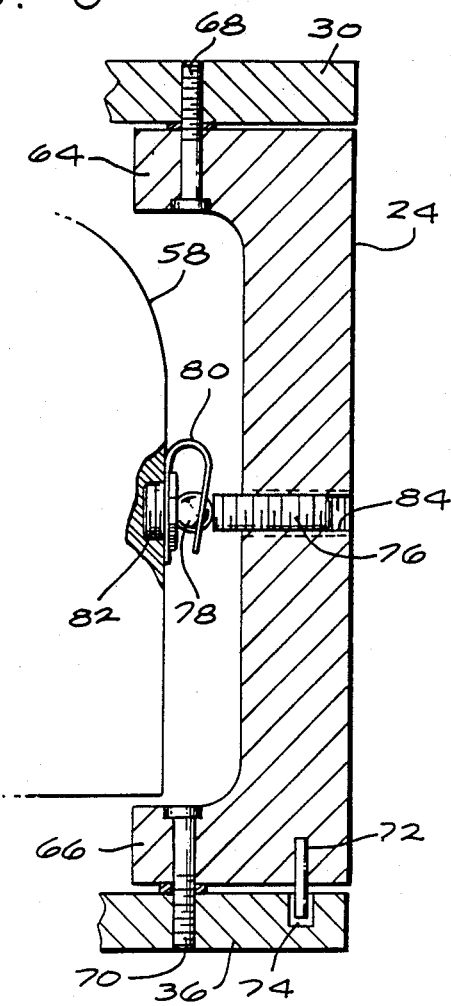
FIG. 6 is an enlarged fragmented vertical sectional view taken generally on the line 6—6 of FIG. 5.
Figure 8:
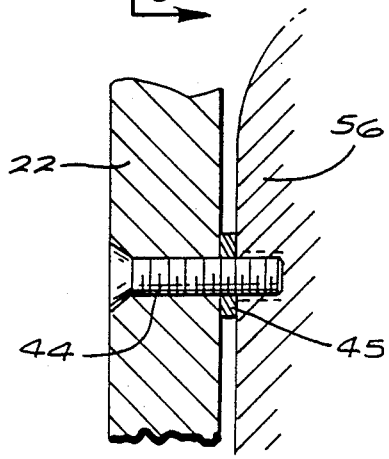
FIG. 8 is an enlarged fragmented vertical sectional view illustrating a preferred mounting an engagement for a force gauge forming a portion of the adduction device.

The load bar 24 is supported at the forward ends of the other two frame links 30 and 36 in a position extending in parallel alongside the reaction arm 58 of the force gauge unit 12. However, the load bar 24 is movably mounted to the frame links 30 and 36 to permit self aligned adaptation of the load bar to compensate for the arcuate nature of the path of swinging motion during adduction movement. More particularly, as shown best in FIGS. 6 and 7, the load bar 24 includes upper and lower feet 64 and 66 projecting in an inboard direction wherein these feet 64 and 66 are pivotally connected to the frame links relative to a vertical pivot axis by a pair of pivot pins 68 and 70. The range of pivoting motion of the load bar 24 is limited by a limit pin 72 at one end of the load bar 24 which is received into an arcuate recessed track 74 formed in the lower frame link 36. This permission of load bar pivoting movement through a limited range of motion maintains the inboard end of a threaded calibration screw 76 on the load bar 24 in engagement with a load ball 78 retained by a cage arm 80 in seated relation upon a load cell platform 82 on the reaction arm 58. For optimum results, this calibration screw is aligned generally with the screw 44 (FIG. 8) fastened into the base member 56. In addition for maintenance of aligned engagement between these components, the pivot axis of the load bar 24 is aligned generally with a centerline of the load ball 78, as viewed in FIG. 6. Moreover, the calibration screw 76 is received into a threaded bore 84 in the load bar 24 with its outboard end exposed to permit calibrating adjustment of screw position. A set screw 86 (FIG. 5) may also be provided for releasably locking the calibration screw in place.

In use, the hand grips 14 and 16 are grasped respectively with the left and right hands of a person (not shown) being tested. While holding the device 10 in front of the body, generally in an upright position in front of the sternum, the hand grips can be pressed together with an adduction force. Importantly, the stop plate 48 prevents sufficient lateral opening of the support bar 22 and load bar 24 to correspondingly prevent release of the load ball 78. Moreover, the stop plate retains the load bar 24 sufficiently close to the load ball 78 to prevent the person being tested from slamming the load bar into the load ball with possible resultant false force reading or damage to the force gauge. Still further, the rotatable mounting of the hand grips 14 and 16 prevents those grips from being subjected to torque loads which could otherwise impact the force reading on the force gauge.

As the person presses the hand grips 14 and 16 toward each other with an adduction force, the load bar 24 is moved in a direction pressing the calibration screw 76 against the load ball 78. Such motion is accompanied by slight pivoting action of the load bar 24 about its associated pivot pins 64 and 66 for maintaining a self-aligned perpendicular relation to the load cell platform 82. Conveniently, rear edge surfaces of the support bar 22 and load bar 24 are conveniently provided with smoothly contoured surfaces, as indicated by arrows 88 in FIG. 2, to avoid striking the hands or fingers with sharp edges of the device during use.

The shoulder strength adduction device 10 of the present invention thus provides a relatively simple apparatus for use in determining upper body strength in individuals. The device provides a direct force reading reflecting the peak static isometric strength of the shoulder musculature, with the elbows and wrists being held relatively taut and thus isolated from the test when the hand grips are subjected to an adduction force.

A variety of further modifications and improvements to the present invention will be apparent to those skilled in the art. Accordingly, no limitation on the invention is intended by way of the foregoing description and the accompanying drawings, except as set forth in the appended claims.

What is claimed is:

1. A shoulder strength adduction device, comprising:
   a pair of generally parallel upright hand grips;
   an upper scissors frame including first and second frame links having rear ends connected respectively to the upper ends of said hand grips;
   a lower scissors frame including first and second frame links having rear ends connected respectively to the lower ends of said hand grips;
   a support bar connected between the forward ends of said first frame links of said upper and lower scissors frames;
   a load bar connected between the forward ends of said second frame links of said upper and lower scissors frames, said load bar being connected to said second frame links to permit rotation of said load bar about a vertical axis; and
   a force gauge unit mounted on said support bar and including reaction means presented toward said load bar for engagement therewith and for movement in response to such engagement upon application of adduction forces to said hand grips, said force gauge unit including means for quantifying and indicating the magnitude of said adduction forces.

2. The shoulder strength adduction device of claim 1 wherein said frame links of said upper and lower scissors frames are pivotally interconnected generally at midpoint positions of said first and second links for each of said upper and lower frames by a common pivot pin, and further including spacer means for maintaining constant vertical spacing between said upper and lower scissors frames.

3. The shoulder strength adduction device of claim 1 further including means for rotatably mounting said hand grips to said scissors frames for rotation of said hand grips respectively about generally parallel vertical axes.

4. The shoulder strength adduction device of claim 3 wherein each of said hand grips includes a cushioned outer grip member.

5. The shoulder strength adduction device of claim 1 wherein said load bar includes a calibration screw extending generally laterally and defining an inboard end presented in direction generally toward said force gauge unit, said reaction means including a reaction arm on said force gauge unit, said reaction arm including a load cell platform having an outboard face presented in a direction generally toward said calibration screw inboard end, and a load ball supported between said calibration screw inboard end and said load cell platform.

6. The shoulder strength adduction device of claim 5 wherein said load bar is pivotally supported by said second frame links of said upper and lower scissors frames for rotation about a generally vertical axis extending generally through the center of said load ball.

7. The shoulder strength adduction device of claim 5 further including means for limiting the range of pivoting motion of said load bar relative to said scissors frames 8. The shoulder strength adduction device of claim 5 wherein said calibration screw is adjustably carried by said load bar.

9. The shoulder strength adduction device of claim 1 further including means for restricting movement of said hand grips to a minor displacement toward and away from each other, said restricting means maintaining said load bar substantially in engagement with said reaction means at all times.

10. A shoulder strength adduction device, comprising:
    a pivoting scissors frame having a forward end and rear end;
    a pair of hand grips mounted to the rear end of said pivoting frame;

a support bar and a load bar mounted to the front end of said pivoting frame, said load bar being supported by said frame for rotation about an axis generally parallel to said hand grips; and a force gauge unit mounted on said support bar, said force gauge unit including reaction means presented generally toward said load bar;, said hand grips being displaceable toward each other through a small stroke to correspondingly displace said support bar and said load bar toward each other, thereby displacing said load bar into bearing engagement with said reaction means, said force gauge unit including means for quantifying and indicating the adduction force of said load bar bearing against said reaction means.

11. The shoulder strength adduction device of claim 10 wherein said hand grips are rotatably mounted on said frame.

12. The shoulder strength adduction device of claim 10 further including means for limiting the movement of said hand grips toward each other to a small stroke such that said load bar in maintained in substantial engagement with said reaction means at all times.

13. The shoulder strength adduction device of claim 10 further including means for limiting the magnitude of rotation of said load bar relative to said frame.

14. A shoulder strength adduction device, comprising:

an upper scissors frame including first and second frame links;

a lower scissors frame including first and second frame links, each of the frame links having forward and rear ends;

pivot pin means for pivotally interconnecting said first and second frame links of said upper frame and for pivotally interconnecting said first and second frame links of said lower frame generally at midpoint positions for rotation about a common vertical axis;

a first hand grip mounted to the rear ends of said first frame links of said upper and lower frames, and a second hand grip mounted to the rear ends of said second frame links of said upper and lower frames, said first and second hand grips being mounted for rotation relative to said frames about generally parallel vertical axes;

a support bar mounted to the forward ends of said first frame links of said upper and lower frames;

a load bar mounted to the forward ends of said second frame links of said upper and lower frames, said load bar being mounted to permit rotation of said load bar about a generally vertical axis relative to said upper and lower frames;

a calibration screw carried by said load bar within a threaded bore formed in said load bar, said calibration screw having an inboard end presented generally toward said support bar; and a force gauge unit mounted on said support bar, said force gauge unit including a force gauge carried by said support bar, a reaction arm movably carried by said support bar in a position generally adjacent said load bar, a load cell platform on said reaction arm and defining an outboard face presented in a direction toward and generally aligned with said calibration screw, and a load ball cooperatively supported between said load cell platform and said calibration screw, whereby adduction displacement of said hand grips toward each other results in a corresponding adduction displacement of said support bar and said load bar toward each other such that said calibration screw applies an adduction force to said load ball to press said load ball against said load cell platform, said reaction arm movably responding to pressing of said load ball against said load cell platform, and said force gauge including means for detecting and quantifying reaction arm movement.

15. The shoulder strength adduction device of claim 14 wherein said load bar is pivotally supported by said upper and lower frames for rotation about a vertical axis passing generally through the center of said load ball.

16. The shoulder strength adduction device of claim 14 further including stop means for restricting pivoting movement of said upper and lower frames to a small angular increment such that said calibration screw and said load cell platform retain said load ball therebetween.

17. The shoulder strength adduction device of claim 14 further including a limit pin mounted on said load bar and received into an arcuate track of limited length formed on one of said second frame links to limit the magnitude of rotation of said load bar relative to said upper and lower frames.

18. A shoulder strength adduction test device, comprising:

a frame including a support bar, a reaction load bar movably mounted with respect to said support bar, a first hand grip, means connecting said first hand grip to said support bar, a second hand grip, means connecting said second hand grip to said reaction load bar, said first and second hand grips being oriented generally in parallel with each other, and said reaction load bar being movable relative to said support bar generally about an axis parallel to said first and second hand grips; and a force gauge unit mounted on said frame and including interengaged first and second cam means mounted respectively on said support bar and said reaction load bar, one of said first and second cam means being movable with respect to the other upon adduction movement of said reaction load bar toward said support bar, said force gauge unit further including means connected to said one of said first and second cam means for quantifying and indicating the adduction force applied to said reaction load bar during such adduction movement.

* * * * *